United States Patent [19]

Hague et al.

[11] Patent Number: 5,543,074

[45] Date of Patent: Aug. 6, 1996

[54] PERSONAL WASHING COMPOSITIONS

[75] Inventors: Jonathon D. Hague, Merseyside; Andrew M. Murray, Cheshire, both of Great Britain

[73] Assignee: Chesebrough-Pond's USA Co., Div. of Conopco, Inc., Greenwich, Conn.

[21] Appl. No.: 389,384

[22] Filed: Feb. 16, 1995

[30] Foreign Application Priority Data

Feb. 18, 1994 [GB] United Kingdom ............... 9403156
Jul. 15, 1994 [GB] United Kingdom ............... 9414332

[51] Int. Cl.$^6$ ................... C11D 3/37; C11D 9/36
[52] U.S. Cl. ............ 510/122; 514/881; 510/125; 510/127; 510/159; 510/417; 510/426; 510/475; 510/466
[58] Field of Search ............ 252/DIG. 13, 174.15, 252/173, 174.23, 174.25, 174.24, 541, 544; 424/70.1, 70.11, 70.12, 70.16, 70.22; 514/881

[56] References Cited

U.S. PATENT DOCUMENTS

| | | |
|---|---|---|
| 2,826,551 | 3/1958 | Geen . |
| 3,580,853 | 5/1971 | Parran, Jr. . |
| 4,299,817 | 11/1981 | Hannan, III et al. . |
| 4,983,383 | 1/1991 | Maksimoski et al. ............ 424/70 |
| 5,037,818 | 8/1991 | Sime . |
| 5,085,857 | 2/1992 | Reid et al. . |
| 5,160,730 | 11/1992 | Dubief et al. ............ 426/59 |
| 5,368,850 | 11/1994 | Cauwet et al. . |

FOREIGN PATENT DOCUMENTS

| | | |
|---|---|---|
| 0219830 | 4/1987 | European Pat. Off. . |
| 0231997 | 8/1987 | European Pat. Off. . |
| 0386898 | 9/1990 | European Pat. Off. . |
| 5160730 | 11/1992 | European Pat. Off. . |
| 0524434 | 1/1993 | European Pat. Off. . |
| 0524434 | 1/1993 | European Pat. Off. . |
| 0529883 | 3/1993 | European Pat. Off. . |
| 2698004 | 11/1992 | France . |
| 2122214 | 1/1984 | United Kingdom . |
| WO92/10162 | 6/1992 | WIPO . |
| WO93/08787 | 5/1993 | WIPO . |
| WO94/21224 | 9/1994 | WIPO . |
| WO95/09599 | 4/1995 | WIPO . |

*Primary Examiner*—Glenn Caldarola
*Assistant Examiner*—Alexander G. Ghyka
*Attorney, Agent, or Firm*—Milton L. Honig

[57] ABSTRACT

Personal washing compositions which contain a cationic deposition polymer of charge density in the range 0.0001 to 0.005 equivalents/gram and average molecular weight greater than $2\times10^6$ daltons in combination with a surfactant to increase deposition of a benefit agent dispersed in the composition onto the skin or hair.

7 Claims, No Drawings

PERSONAL WASHING COMPOSITIONS

BACKGROUND OF THE INVENTION

1. Field of the Invention

This invention relates to personal washing compositions which contain a cationic deposition polymer to increase deposition of a benefit agent onto the skin or hair.

2. The Related Art

For many years it has been known that hair can be conditioned by incorporation of silicone in a shampoo composition. U.S. Pat. No. 2,826,551 (Geen) is typical of an early disclosure of such 2 in 1 shampoos. Various attempts have been made to improve the efficiency of use of the expensive silicone component. This would provide better conditioning and the option of reducing the level of expensive benefit agent in the shampoo, with consequent cost saving.

Deposition polymers with a cationic charge have been proposed to enhance the amount of benefit agent deposited from the shampoo. For example cationic guar gum has been described for the enhancement of the deposition of antidandruff particles in U.S. Pat. No. 5,037,818 and for the enhanced deposition of insoluble non-volatile silicone in U.S. Pat. No. 5,085,857. The use of cationic polymers in shower gels to enhance deposition of silicone oil is also known from EP-A-457 688 (L'Oreal).

Deposition polymers have also been proposed to enhance the deposition of sunscreen materials from a shampoo composition. In EP 386 898 a cationic polygalactomannan gum derivative is used.

Polyacrylamides have been proposed for use in shampoos in EP 0 231 997. These polymers are not charged and do not assist in the deposition of benefit agents.

When washing with any of the prior art systems a considerable amount of the benefit agent will be rinsed away with the composition, and there is scope for substantially improving the deposition efficiency.

It is an object of the present invention to provide a more efficient deposition polymer than the previously described polygalactomannan polymers.

SUMMARY OF THE INVENTION

According to the present invention there is provided a personal washing composition comprising: a surface active agent selected from anionic, nonionic, zwitterionic and cationic surfactants, soap and mixtures thereof, water, a non-volatile insoluble benefit agent dispersed in the composition and from 0.001 to 1% by weight of a deposition polymer which is a cationic copolymer wherein the charge density of the copolymer is in the range 0.0001 to 0.005 eq/g, preferably 0.0008 to 0.0025 eq/g; and the average molecular weight of the copolymer is more than $2 \times 10^6$ daltons.

Preferably the amount of deposition polymer lies in the range 0.05 to 0.2% by weight. Preferably the cationic copolymer is a copolymer of acrylamide and a cationic monomer having the formula:

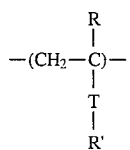

where: T is —O— or

R is H or $CH_3$ and R' is $-NH-(CH_2)_n-N^+(CH_3)_3\ X^-$ or $-O-(CH_2)_n-N^+(CH_3)_3\ X^-$ in which n is an integer from 1 to 4 and X is selected from Cl, Br, I and $CH_3SO_3$.

DETAILED DESCRIPTION OF THE INVENTION

The composition is suitable for cleansing and conditioning of the skin or hair. The term "conditioning" is intended to cover "moisturising" and "protection".

Throughout this specification reference to average molecular weight (Mw) means a molecular weight calculated as follows.

The intrinsic viscosity of a polymer may be determined by standard capillary viscometry. The viscosity of a series of low polymer concentrations in a given solvent is determined relative to the pure solvent. The relative viscosity $N_r$ is defined as:

$$N_{polymer\ sol}/N_{solvent}$$

The specific viscosity $N_{sp}$ is:

$$N_r - 1$$

If $N_{sp}/c$, where c is the polymer concentration, is plotted against c, a straight line is usually obtained. The point at which the straight line crosses the y intercept is the intrinsic viscosity ($N_{in}$). This is related to the coil size of the polymer.

The intrinsic viscosity can also be related to the molecular weight of the polymer if the Mark-Houwink parameters are known. Thus, $$N_{in} = K(Mw)^a$$

Where K and a are the Mark-Houwink parameters.

These have been determined for polyacrylamide, and also for a number of copolymers of acrylamide and N,N,N trimethylaminoethyl chloride acrylate. These polymers are in accordance with those found useful in the present invention. The parameters can be found in Mabire et al, Polymer 1984 (25) 1984.

For CPA1, CPA2 and CPA5 to 10 we used the MH parameters for 30% cationic polymer. For CPA 3 and CPA 4 we used MH parameters for acrylamide homopolymer. Whichever is used, the Mw figure is approximately the same. Thus, if the MH parameters for acrylamide are used for CPA 1, the Mw figure becomes 5,000,000 rather than 8,000,000.

There is a precedent in the scientific literature where an estimate of Mw has been made for cationic polyacrylamides by using the MH parameters for acrylamide homopolymer: Hubbe, M. A., Colloids and Surfaces 1987 25 p. 325.

The MH parameters are generated for 1M NaCl, so, in accordance with normal practice for polyelectrolytes, 1M NaCl was used as a solvent for our measurements. Intrinsic viscosity of some of the polymers used is given below:

| Polymer | Intrinsic Viscosity (dl/g) 1M NaCl |
|---|---|
| CPA 1 | 11.1* |
| CPA 2 | 1.1* |
| CPA 3 | 11.8 |
| CPA 4 | 1.2 |
| CPA 5 | 12.5 |
| CPA 6 | 8.0 |
| CPA 7 | 2.8 |
| CPA 8 | 10.4 |
| CPA 9 | 6.9 |
| CPA 10 | 8.25 |
| JR 400 | 4.8 |
| JR 30M | 12.0 |
| Jaguar C13S | 9.8 |
| Merquat 550 | 2.7 |

"CPA" polymers are copolymers of acrylamide and N,N, N-trimethyl aminopropylacrylamide. CPA 1, 2, 5, 7, 9 and 10 have cationic charge densities of 0.00145 eq/g. CPA 3 and CPA 4 have cationic charge densities of 0.0004 eq/g. CPA 6 and CPA 8 have respective cationic charge densities 0.00194 and 0.0009 eq/g. All CPA copolymers were ex Allied colloids. The Intrinsic viscosities for CPA 1, 2 and 5 to 10 is data from Allied Colloids. The data for CPA3 and CPA4 was produced by the above method and corresponds closely with the data supplied by Allied Colloids for these materials.

Preferred "CPA" polymers have an intrinsic viscosity of at least 7.

By "benefit agent" is meant a protective and/or softening substance that maintains softness by retarding the decrease in water content from the skin (stratum corneum) or hair.

Normally the benefit agent is an oil. For skin, preferred benefit agents include a) silicone oils, gums and modifications thereof such as linear and cyclic polydimethylsiloxanes; amino, alkyl alkylaryl and aryl silicone oils;

b) fats and oils including natural fats and oils such as jojoba and beef tallow;

c) waxes such as beeswax and lanolin;

d) hydrocarbons such as petrolatum and mineral oil;

e) higher fatty acids and higher fatty alcohols, both saturated and unsaturated, having a carbon chain length in the range $C_{12}$ to $C_{22}$;

f) esters such as isopropyl myristate and isopropyl palmitate;

g) essential oils such as evening primrose oil;

h) lipids such as cholesterol, ceramides, sucrose esters and pseudo-ceramides as described in European Patent Specification No. 556 957;

i) vitamins such as vitamin A and E, and vitamin alkyl esters, including those vitamin C alkyl esters;

j) sunscreens such as octyl methoxyl cinnamate (Parsol MCX) and butyl methoxy benzoylmethane (Parsol 1789); and k) mixtures of any of the foregoing components.

For hair, the oil may take the form of a sunscreen, a styling or bodying agent or a conditioning oil. Among suitable sunscreens and other benefit agents there may be mentioned: the group of branched hydrocarbon materials of high molecular weight referred to elsewhere as peralk(en)yl hydrocarbons. These may be either in an organic solvent or directly emulsified in the shampoo composition to give styling or bodying effects. Polyisobutene is a preferred branched hydrocarbon material. Also oil soluble sunscreens partitioned into emulsified oil droplets. Among the oils suitable for this purpose are phenyl silicones and among the suitable sunscreens are, benzophenone compounds, dibenzoyl methane derivatives and camphor derivatives. A preferred sunscreen material is a UV absorber such as 2-ethyl hexyl methoxy cinnamate sold under the trade name Parsol MCX by Givaudan.

Silicone oil is a preferred conditioning oil for skin or hair. The silicone may be in the form of a low viscosity oil which may contain a high viscosity oil or gum in solution. Alternatively the high viscosity material may be in the form of an emulsion in water. The emulsion may be of high viscosity oil or of a solution of gum in a lower viscosity oil. The particle size of the oil phase may be anywhere in the range from 30 nanometres to up to 20 microns average size.

When the oil is a silicone it may be a polydimethylsiloxane with an average particle size of less than 20 microns and preferably less than 2 microns. Small particle size enables a more uniform distribution of silicone conditioning agent for the same concentration of silicone in the composition. Advantageously a silicone with a viscosity in the range 1–20 million cst is used. The silicone can be cross-linked.

The personal washing composition may further comprise from 0.1 to 5% of a suspending agent selected from polyacrylic acids, cross linked polymers of acrylic acid, copolymers of acrylic acid with a hydrophobic monomer, copolymers of carboxylic acid- containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Ethylene glycol distearate and Polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. The suspending agent is particularly preferred when silicone is present.

Suitable cross linked polymers of acrylic acid and acrylate esters are Pemulen TR1 or Pemulen TR2. A suitable heteropolysaccharide gum is xanthan gum, for example that available as Kelzan mu.

In skin washing compositions of the invention, the surface active agent can be selected from any known surfactant suitable for topical application to the human body. Mild surfactants, ie. surfactants which do not damage the stratum corneum, the outer layer of skin, are particularly preferred.

One preferred anionic surfactant is fatty acyl isethionate of formula:

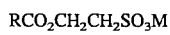

$$RCO_2CH_2CH_2SO_3M$$

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic surfactant is alkyl ether sulphate of formula:

$$RO(CH_2CH_2O)_nSO_3M$$

where R is an alkyl group of 8 to 22 carbon atoms, n ranges from 0.5 to 10 especially 1.5 to 8, and M is a solubilising cation as before.

Other possible anionic surfactants include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula: $R^5O_2CCH_2CH(SO_3M)CO_2M$; and amido-MEA sulphosuccinates of the formula: $RCONCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein R ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Mixtures of any of the foregoing surface active agents may also be used.

It is also preferable that the composition includes at least one cosurfactant agent with skin-mildness benefits. Suitable materials are zwitterionic detergents which have an alkyl or alkenyl group of 7 to 18 carbon atoms and comply with an overall structural formula $$R^1 + \overset{O}{\overset{\|}{C}} - NH(CH_2)_m \underset{n}{]} \overset{R^2}{\underset{R^3}{\overset{|}{N^+}}} - X - Y$$

where $R^1$ is alkyl or alkenyl of 7 to 18 carbon atoms $R^2$ and $R^3$ are each independently alkyl, hydroxyalkyl or carboxyalkyl of 1 to 3 carbon atoms
m is 2 to 4
n is 0 or 1
X is alkylene of 1 to 3 carbon atoms optionally substituted with hydroxyl, and Y is $-CO_2^-$ or $-SO_3^-$ Zwitterionic detergents within the above general formula include simple betaines of formula:

$$R^1 - \overset{R^2}{\underset{R^3}{\overset{|}{N^+}}} - CH_2CO_2^-$$

and amido betaines of formula:

$$R^1 - CONH(CH_2)_m - \overset{R^2}{\underset{R^3}{\overset{|}{N^+}}} - CH_2CO_2^-$$

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is a sulphobetaine of formula:

$$R^1 - \overset{R^2}{\underset{R^3}{\overset{|}{N^+}}} - (CH_2)_3SO_3^-$$

or $$R^1 - CONH(CH_2)_m\overset{R^2}{\underset{R^3}{\overset{|}{N^+}}} - (CH_2)_3SO_3^-$$

where m is 2 or 3, or variants of these in which $-(CH_2)_3SO_3^-$ is replaced by $$-CH_2\overset{OH}{\overset{|}{C}H}CH_2SO_3^-$$

$R^1$, $R^2$ and $R^3$ in these formulae are as defined previously.

The surface active agent is preferably present in amount of from 2 to 40% by weight, and preferably from 5 to 30% by weight. The cosurfactant, is present, is preferably present at a level of 0.5 to 15% by weight.

The skin washing composition according to the invention may also include minor amounts of other ingredients such as antibacterial agents, foam boosters, pearlescers, perfumes, dyes, colouring agents, preservatives, thickeners, proteins, other polymers, phosphate esters and buffering agents.

Shampoo compositions of the invention contain anionic surfactant together with optional nonionic and amphoteric surfactant.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally contains from 8 to 18 carbon atoms and may be unsaturated. The alkyl ether sulphates, alkyl ether phosphates and alkyl ether carboxylates may contain from one to 10 ethylene oxide or propylene oxide unites per molecule, and preferably contain an average of 2 to 3 ethylene oxide units per molecule.

Further examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in the shampoo compositions of the invention include condensation products of aliphatic ($C_8$–$C_{18}$) primary or secondary linear or branched chain alcohols or phenols with alkylene oxides, usually ethylene oxide and generally 6–30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutameates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

The surfactants are present in the shampoo compositions of the invention in an amount of from 2 to 40% by weight, and preferably from 5 to 30% by weight.

The shampoo may also include minor amounts of other ingredients such as antibacterial agents, foam boosters, pearlescers, perfumes, dyes, colouring agents, preservatives, thickeners, proteins, other polymers, phosphate esters and buffering agents.

The invention will now be described, with reference to the following non-limiting examples:

[A] Skin Washing Compositions

EXAMPLES

In the examples:
Coco amidopropyl betaine was Tergobetaine F ex Goldschmidt or Amonyl BA 380 ex Seppic.
Guar hydroxypropyl trimonium chloride was Jaguar C-13-S ex Meyhall.
Silicone oil emulsion was BC 89/138 ex Basildon.
Sodium cocoyl isethionate was either Jordapon CI ex PPG/Mazer or Hostapan SCI ex Hoechst.
Sodium lauryl ether sulphate was Genapol ZRO ex Hoechst.

Compositions according to the invention and comparative compositions were tested by the following method.

A number of tests were carried out by human volunteers. The experimental procedure employed was as follows:

The volunteers washed their forearms with a shower gel. The procedure involved wetting the arm and also the volunteer's free hand with warm water then using the free hand to lather the arm with 0.5 grams of the shower gel, next rinsing for 10 seconds while rubbing with the free hand and then drying the arm with a single pass with a paper towel.

10 minutes after drying the forearm a strip of adhesive tape is pressed onto the areas on the forearms keeping it in place for 30 seconds using a spring loaded device bearing on a rubber bung to press the tape onto the skin with a repeatable pressure of 85 g.cm$^{-2}$. The adhesive tape employed was J-Lar Superclear (TM) tape having a width of 25 mm. Two strips of tape are applied to each forearm in this way to adjacent areas of the skin.

In this test procedure silicone which has deposited on the skin is transferred to the tape along with some of the outer layer of the volunteer's skin.

The amounts of silicon and skin adhering to the tape are determined by means of X-ray fluorescence spectroscopy. The tape strips are placed in an X-ray fluorescence spectrometer with the adhesive side facing the beam of this machine. A mask is applied over the tape to define a standardised area in the middle of the tape which is exposed to the X-ray beam. The sample chamber of the machine is placed under vacuum before making measurements and the spectrometer is then used to measure the quantities of silicon and sulphur. The sulphur is representative of the amount of skin which has transferred to the tape. Results are presented in terms of the ratio of Si:S.

EXAMPLE 1

In this example deposition of silicone from compositions containing a range of polymers according to the invention was compared with deposition from a composition containing a polymer which is a commercially available shower gel, namely, guar hydroxypropyl trimonium chloride (comparison).

The base formulation was:

|  | % wt |
| --- | --- |
| Sodium lauryl ether sulphate (SLES) | 13.00 |
| Coco amidopropyl betaine (CAPB) | 2.00 |
| Silicone oil emulsion | 5.00 |
| Sorbic acid | 0.37 |
| Sodium citrate dihydrate | 0.49 |
| Sodium chloride | 2.0 |
| Citric acid | 0.01 |
| Water + minors | to 100 |

Polymers were added to the base formulation at a level of 0.1% wt.

Each composition was prepared by forming a 1% dispersion of the polymer by adding it to water at ~50° C. SLES and CAPB were added to the excess water of the formulation with gentle stirring. Thereafter the silicone oil emulsion was added with stirring to the surfactant mixture. This was followed by the polymer dispersion and finally the minors. Deposition of silicone was determined according to the procedure described above, The Si:S ratio for the comparison was normalised to 1 and the values for the compositions according to the invention expressed relative to the comparison.

The following results were obtained:

| Polymer | Si:S |
| --- | --- |
| Comparison | 1 |
| CPA 6 | 4.19 |
| CPA 1 | 2.42 |
| CPA 7 | 1.90 |

The results demonstrate. the improved deposition obtained with the compositions according to the invention.

In a further set of experiment with the same base formulation but with different polymers the following results were obtained.

| Polymer | Si:S |
| --- | --- |
| Comparison | 1 |
| CPA 9 | 1.83 |
| CPA 10 | 2.10 |
| CPA 5 | 2.81 |
| CPA 8 | 1.72 |

These results also demonstrate the improved deposition obtained with the compositions according to the invention.

EXAMPLE 2

In this example the variation of silicone deposition with the amount of polymer added to the base formulation was examined and compared with that from a composition containing no polymer.

The base formulation was:

|  | % wt |
|---|---|
| Sodium lauryl ether sulphate | 2.00 |
| Coco amidopropyl betaine (CAPB) | 8.00 |
| Sodium cocoyl isethionate | 5.00 |
| Silicone oil emulsion | 5.00 |
| Water + minors | to 100 |

It was prepared by forming a premix of the cocoyl isethionate (25% dispersion) by adding it to water at 45° C. The SLES and isethionate premix were then added to the excess water of the formulation with gentle stirring, followed by the CAPB. Thereafter the silicone oil emulsion was added with stirring. A 1% dispersion of the polymer was prepared by adding it to water at ~50° C. This was then added to the surfactant/silicone mixture to the required level followed by the minors.

Deposition of silicone was determined according to the procedure described above.

The following results were obtained:

| Polymer | % wt | Si:S |
|---|---|---|
| Comparison | 0 | 0.41 |
| CPA 5 | 0.05 | 1.02 |
|  | 0.1 | 2.43 |
|  | 0.2 | 3.28 |
| Comparison | 0 | 0.36 |
| CPA 6 | 0.05 | 2.95 |
|  | 0.1 | 4.28 |
|  | 0.2 | 4.16 |

The results demonstrate that silicone deposition increases as the amount of polymer present in the composition increases.

[B] Shampoo Compositions

Test of Conventional Cationic Polymers

Many of the commercially available cationic polymers designed for use in cosmetics show no ability to deposit silicone on to hair during the course of the hair washing/rinsing cycle. Table 1 details the performance of a range of cationic polymers promoted by their manufacturers as suitable for use in shampoo applications. The polymers were tested as silicone deposition and retention aids in one of the shampoo formulations (A,B,C or D) given below in Table 3.

TABLE 1

| Eg | Polymer | shampoo | silicone retention on hair ppm | % deposition | polymer Mw |
|---|---|---|---|---|---|
| A | C13S | C | 1280 | 26 | 250 000 |
| B | C13S | A | 983 | 20 | 250 000 |
| C | C15 | A | 142 | 3 | <100 000 |
| D | C13S | D | 1828 | 25 | 250 000 |
| E | JR400 | A | 0 | — | 400 000 |
| F | JR30M | A | 0 | — | 600 000 |
| G | JR400 | B | 661 | 14 | 400 000 |
| H | JR400 | C | 0 | — | 400 000 |
| I | FC370 | A | 0 | — | 100 000 |
| J | Quat-PVA | A | 0 | — | 125 000 |

TABLE 1-continued

| Eg | Polymer | shampoo | silicone retention on hair ppm | % deposition | polymer Mw |
|---|---|---|---|---|---|
| K | 550 | A | 0 | — | 700 000 |
| L | — | A | 0 | — | — |
| M | — | C | 0 | — | — |

A figure of zero for silicone retention indicates that the amount detected was negligible and could not accurately be measured.

C13S is JAGUAR (trade mark) C13S, a cationic guar derivative ex Meyhall
C15 is JAGUAR C15, also a cationic guar derivative ex Meyhall
JR400 is POLYMER JR400, a polysaccharide derivative ex Union Carbide
JR30M is POLYMER JR30M, a polysaccharide derivative ex Union Carbide
FC370 is Luviquat FC 370(trade mark), ex BASF
Quat-pva is a copolymer prepared by reacting glycidyltrimethylammonium chloride with a commercial PVA; Mowiol 40–88, ex Hoeschst. The molecular weight (Mw) is 127,000 (supplier's data). The final charge density (from NMR) is 1.2 meq/g.
550 is Merquat 550 ex Croxton and Garry.

Of these examples, only example K is polyacrylamide based. The value given for polymer Mw in the table is suppliers data for all examples except Example K. According to Croxton+Garry, Merquat 550 has a weight average molecular weight of 2.8 million, however, when measured using our Intrinsic viscosity method a value for Mw of 700 000 is obtained.

All retention figures were obtained direct from hair switches washed twice for 30s, and rinsed twice for 30s, in running tap water. Shampoo application was at the level of 0.12 g/g hair. Silicone levels were determined from X-Ray Fluorescence count rates by comparison with known standards.

Silicone retention efficiency from formulations containing these low Mw polymers does not exceed 25%.

EXAMPLES 3–8 HIGH MOLECULAR WEIGHT CATIONIC POLYACRYLAMIDES

Using high molecular weight polyacrylamides (Mw>3,000,000) gives previously unattainable levels of silicone retention, typically far in excess of 50% efficiency. The results are shown in Table 2.

TABLE 2

| Example | Polymer | Shampoo | Silicone retention ppm | Efficiency % | Mol wt |
|---|---|---|---|---|---|
| 3 | CPA1 | D | >5000 | >70 | 8 000 000 |
| 4 | CPA1 | A | 2060 | 43 | 8 000 000 |
| 5 | CPA2 | A | 0 | — | 400 000 |
| 6 | CPA3 | C | 63 | 63 | 6 000 000 |
| 7 | CPA4 | C | 130 | 3 | 220 000 |
| 8 | '703 | A | >>2500 | >>55 | >5 000 000 |

Thus, although most commercially available cationic polymers with Mw below 1,000,000 intended for use in cosmetic products show little or no activity as deposition aids from conventional shampoo formulations, use of very high Mw (>3,000,000) cationic polyacrylamides in shampoo formulations gives surprisingly increased levels of silicone retention.

TABLE 3

SHAMPOO A:

| | |
|---|---|
| 16 | SLES 2EO |
| 2 | Lauryl Betaine |
| 2.25 | Ethylene glycol distearate |
| 4 | BY22-026 (50% silicone emulsion) ex Toray silicone |
| 0.1 | Deposition Polymer as specified |

SHAMPOO B:

| | |
|---|---|
| 8 | SLES 3EO |
| 4 | cocoamido propylbetaine |
| 1.5 | NaCl |
| 4 | BY22-026 |
| 0.3 | Deposition Polymer as specified |

SHAMPOO C:

| | |
|---|---|
| 2 | SLES 2EO |
| 2 | BY22-026 |
| 0.1 | Deposition Polymer as specified |

SHAMPOO D:

| | |
|---|---|
| 6 | SLES 2EO |
| 2 | cocoamido propylbetaine |
| 1.5 | ethylene glycol distearate |
| 0.5 | Potassium sorbate |
| 0.25 | Citric Acid |
| 4.8 | X2-1766 (60% Silicone emulsion) ex Dow Corning |
| 0.3 | NaCl |
| 0.1 | Deposition Polymer as specified |

Comparative Examples N and O

Because we believed that the higher charge density Jaguar C17 might out perform the Jaguar C13S tested in Examples A, B and D, we made a comparison between C17 and other polymers in shampoo A as follows:

Example N: Shampoo A with Jaguar C13S 983 ppm 20% efficiency

Example O: Shampoo A with Jaguar C17l 413 ppm 29% efficiency

The polyacrylamides with high molecular weight (Examples 1,2,4 and 6) clearly outperform Jaguar C17.

The silicone level in these shampoos was 2% by weight.

EXAMPLE 9 AND COMPARATIVE EXAMPLES P AND Q

To show that the deposition polymers according to the invention can give benefit when added to a commercial shampoo we tested "Wash and Go" Dry Sensitive, (Comparative Example P believed to be without deposition polymer) and "Wash and Go" Extra Conditioning (Comparative Example Q, believed to be with Jaguar C17) against the "Dry Sensitive" formulation with 0.2% CPA1 added, (Example 7). CPA1 is a copolymer of acrylamide and N,N,N-trimethylaminopropylacrylamide. "Wash and Go" is a range of 2 in 1 shampoos sold by Procter & Gamble based on an alkyl sulphate and ether sulphate anionic surfactant mixture. The increased deposition from use of the deposition polymer according to the invention is readily apparent.

Deposition of silicone (ppm silicone) was measured by X-Ray Fluorescence:

Example P 562 +/−289 ppm
Example Q 468 +/−103 ppm
Example 7 1630 +/−635 ppm

All figures are an average from 5 hair samples. It can be seen that addition of the Polymer according to the invention trebles the efficiency of silicone deposition.

We claim:

1. An aqueous personal washing composition comprising:
   a) 2 to 40% by weight of a surface active agent selected from the group consisting of anionic, nonionic, zwitterionic and cationic surfactants, soap and mixtures thereof;
   b) a non-volatile insoluble benefit agent dispersed in the composition present in an effective amount to condition hair or skin, the benefit agent being selected from the group consisting of silicone oils and hydrocarbons; and
   c) from 0.001 to 1% by weight of a deposition polymer which is a cationic copolymer wherein the charge density of the copolymer is in the range 0.0001 to 0.005 equivalents/gram, the average molecular weight of the copolymer is more than $2 \times 10^6$ daltons and the cationic polymer is a copolymer of acrylamide and a cationic monomer having the formula:

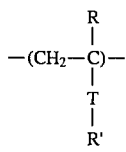

where: T is —O— or

R is H or $CH_3$ and $R^1$ is —NH—$(CH_2)_n$—$N^+(CH_3)_3 X^-$ or —O—$(CH_2)_n$—$N^+(CH_3)_3 X^-$ in which n is an integer from 1 to 4 and x is selected from Cl, Br, I and $CH_3SO_3$.

2. A composition according to claim 1 in which the amount of deposition polymer lies in the range 0.05 to 0.2% by weight.

3. A composition according to claim 1 in which the charge density of the deposition polymer lies in the range 0.0008 to 0.0025 eq/g.

4. A composition according to claim 1 in which the benefit agent is a silicone oil.

5. A composition according to claim 6 in which the composition further comprises from 0.1 to 5 % of a suspending agent for the silicone oil selected from the group consisting of polyacrylic acids; cross linked polymers of acrylic acid; copolymers of acrylic acid with a hydrophobic monomer; copolymers of carboxylic acid- containing monomers and acrylic esters; cross-linked copolymers of acrylic acid and acrylate esters; heteropolysaccharide gums; crystalline long chain acyl derivatives; fatty acid monoglyceride polyglycol ethers; propylene glycol and propylene glycol oleate; and mixtures thereof.

6. A composition according to claim 1 which is a shampoo composition and in which the surface active agent is an anionic surfactant.

7. A shampoo composition according to claim 6 in which the anionic surfactant is selected from the group consisting of sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO and mixtures thereof.

* * * * *